United States Patent
Goll

(10) Patent No.: US 6,860,113 B2
(45) Date of Patent: Mar. 1, 2005

(54) APPARATUS FOR CONTROLLING A MICROTOME AND A COOLING CHAMBER PROVIDED THEREFOR

(75) Inventor: Hubert Goll, St. Poelten (AT)

(73) Assignee: Leica Mikrosysteme GmbH, Vienna (AT)

( * ) Notice: Subject to any disclaimer, the term of this patent is extended or adjusted under 35 U.S.C. 154(b) by 0 days.

(21) Appl. No.: 10/660,142

(22) Filed: Sep. 11, 2003

(65) Prior Publication Data

US 2004/0050074 A1 Mar. 18, 2004

(30) Foreign Application Priority Data

Sep. 13, 2002 (DE) .......................................... 102 42 712

(51) Int. Cl.[7] .............................................. F25B 49/00
(52) U.S. Cl. .......................................... 62/126; 62/320
(58) Field of Search ......................... 62/125, 126, 129, 62/320

(56) References Cited

U.S. PATENT DOCUMENTS

| | | | | |
|---|---|---|---|---|
| 3,204,424 A | * | 9/1965 | McCormick et al. | ......... 62/320 |
| 4,979,376 A | * | 12/1990 | Biehl et al. | .................... 62/264 |
| 5,048,300 A | * | 9/1991 | Lihl | ............................ 62/48.1 |
| 5,533,342 A | * | 7/1996 | Gordon | ....................... 62/51.1 |
| 6,178,757 B1 | | 1/2001 | Sitte et al. | ..................... 62/126 |

OTHER PUBLICATIONS

Brochure Leica CM3050 S *The new versatile cryostat for research and routine histology.*
Brochure Leica CM3600 *Cryomacrotome for pharmaceutical and biomedical research.*
Brochure Reichert Ultracut S/FCS *Ultramicrotome and Cryo–Sectioning System.*
Brochure Leica CM 3600 *A new dimension in cryosectioning technology.*
Brochure, Microm, HM 505E, HM 505N, "A new class of standard cryostats for research and routing use".
Brochure, Microm, HM 500 Series, "Universal cryostat microtomes".
Brochure, Leica, Jung CM 3000, "Modular cryostat system".
Brochure, Leica, Leica CM 3050, "Technology and ergonomics at the highest level".

* cited by examiner

*Primary Examiner*—William E. Tapolcai
(74) *Attorney, Agent, or Firm*—Houston Eliseeva LLP

(57) ABSTRACT

An apparatus for controlling a microtome (2) and a cooling chamber (4) provided therefor is disclosed. Control is accomplished by way of a single control unit (12, 18) that integrates both operating elements (30) for the microtome (2) and operating elements (32) for the cooling chamber (4).

6 Claims, 3 Drawing Sheets

APPARATUS FOR CONTROLLING A MICROTOME AND A COOLING CHAMBER PROVIDED THEREFOR

CROSS REFERENCE TO RELATED APPLICATIONS

This application claims priority of the German patent application 102 42 712.7 which is incorporated by reference herein.

FIELD OF THE INVENTION

The present invention concerns an apparatus for controlling a microtome and a cooling chamber provided therefor.

BACKGROUND OF THE INVENTION

U.S. Pat. No. 6,178,757 describes a control apparatus for a cooling chamber into which a microtome or ultramicrotome is placed. The control apparatus encompasses a microcontroller to which a first and a second control circuit for the sample and the knife are connected. An adjusting element is provided for adjusting and also correspondingly monitoring the desired temperature for the knife and sample.

Control of a system that comprises a microtome and a cooling chamber is described in the brochure for the Leica Ultracut S/FCS. There are two separate control units for the overall system. A first control unit is used for control purposes and for the input of cutting parameters for the microtome. The second control device serves exclusively for adjustment and temperature regulation of the cooling chamber around the region of the knife and the sample holder. Since the space available on laboratory benches is usually limited, a plurality of control units is not necessarily especially suitable.

In order to solve the problem of insufficient space, the RCM company proposes, in its company brochure, the variant of a small cooling chamber control unit. This control unit can be placed on the ultramicrotome control unit. Nevertheless, two separate control units are still provided, and the power supply and power electronics for the cooling chamber control unit are additionally housed in a "black box." This additional black box need not be placed on the laboratory bench, since it contains no operating elements. An additional part of a system is created, however, which is not conducive to user-friendliness.

The Leica CM 3600 discloses a sectioning device for large biological tissues. There is a programmable logic unit controller provided which allows input of study related data. The Leica CM 3600 does not disclose two separate units which are controlled by one control device.

The Leica CM 3050 S shows a cryostat system which can produce slices at low temperatures. The difference to the present invention is that the whole system is covered with a temperature shielding housing and the housing itself includes control buttons.

SUMMARY OF THE INVENTION

It is therefore the object of the invention to create a unified, space-saving, and user-friendly control system for a system made up of a microtome and a separate cooling chamber.

The object is achieved, according to the present invention, with an apparatus for controlling a microtome and a cooling chamber, which is positioned on the microtome, comprising:

a single control unit that integrates both operating elements for the microtome and operating elements for the cooling chamber; and a single display is associated with the control unit, wherein the single display is, dependent from the specific configuration of microtome and cooling chamber, a user interface for the microtome and/or the cooling chamber.

The apparatus for controlling a microtome and a cooling chamber provided therefor has the critical advantage that a single control unit is provided that integrates both operating elements for the microtome and operating elements for the cooling chamber. Associated with the control unit is a user interface that is embodied in the form of a display or screen. The operating elements can be presented to a user on the display. The control unit is configured in such a way that a cooling chamber connected to the microtome can be detected. The control unit modifies or adds to the operating elements presented on the display in accordance with the operating elements for the cooling chamber.

It is particularly advantageous that the invention results not only in space reduction on a laboratory bench, but also in simpler handling for the user. It is likewise advantageous and conceivable for functions that are not often used to be presented only in a submenu on the display. The result of this is that the control unit is arranged and/or organized better.

The power electronics and/or power supplies, which are not housed in this control unit, can be assigned to the devices (microtome or cooling chamber). A black box or an external power supply is also conceivable. It is furthermore advantageous that the invention not only achieves the space reduction, but also makes possible a cost reduction. This is important principally for customers who do not originally possess a cooling chamber, since the control unit has cooling-chamber costs associated with it.

BRIEF DESCRIPTION OF THE DRAWINGS

The invention will be elucidated below with reference to the examples depicted schematically in the Figures, in which.

DETAILED DESCRIPTION OF THE INVENTION

Figure 1:
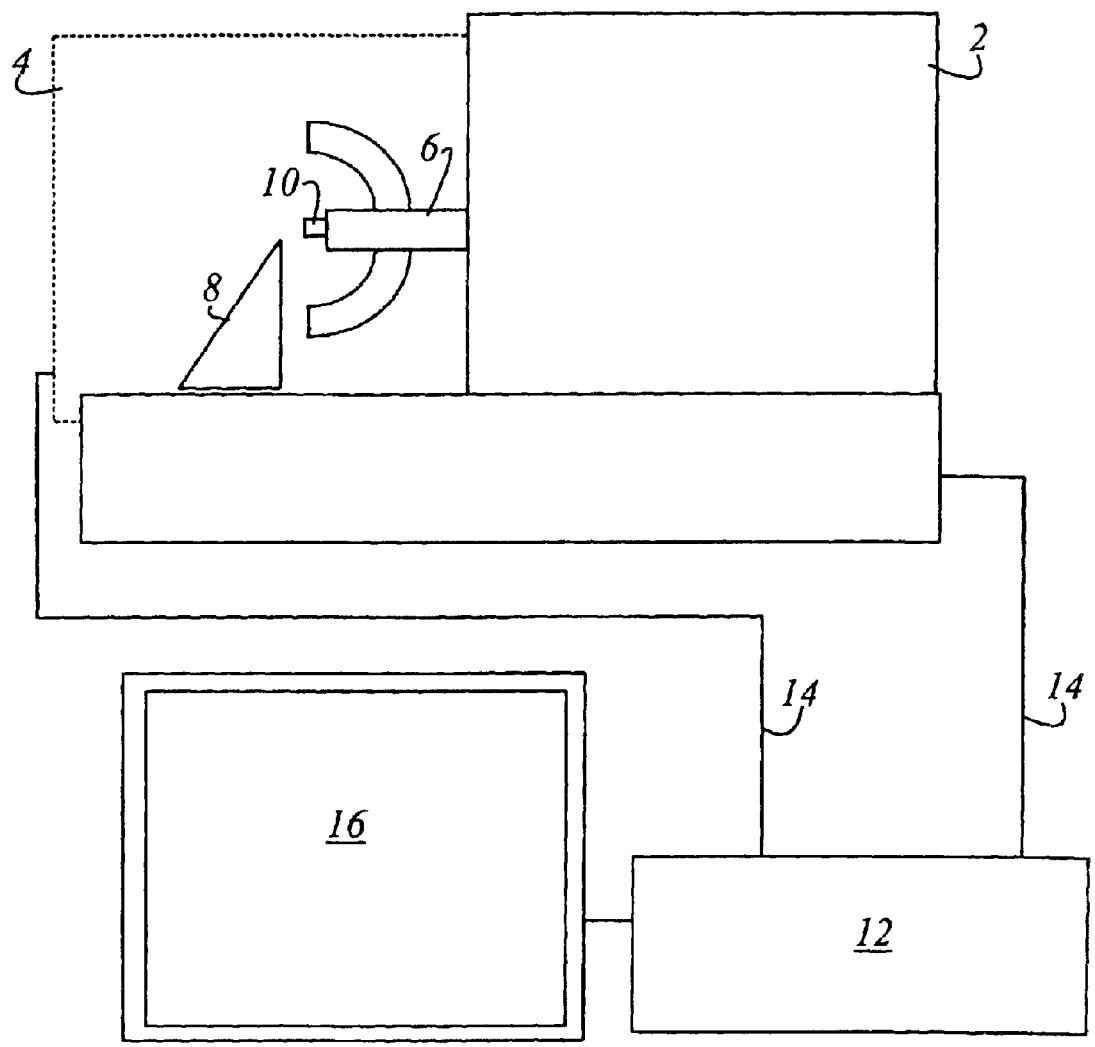
FIG. 1 is a schematic side view of the microtome with a cooling chamber and control unit.
Figure 2:
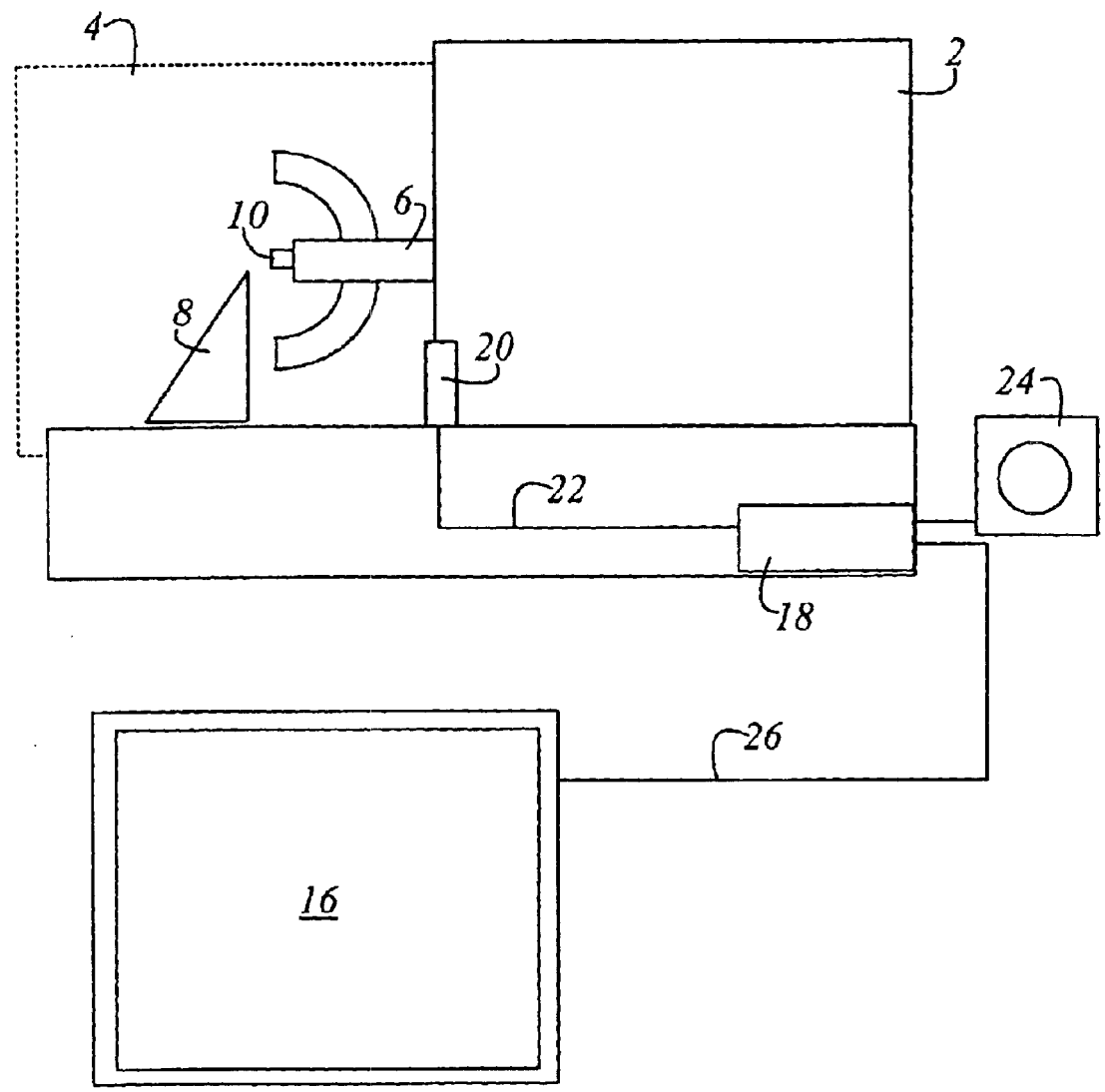
FIG. 2 is a schematic side view of another embodiment of the microtome with cooling chamber and control unit.

FIG. 1 is the a schematic side view of a microtome 2 that is equipped with a cooling chamber 4. Although only the term "microtome" is used in the foregoing description and in the description to follow, this term is also, of course, understood to mean an ultramicrotome. In the depiction of FIGS. 1 and 2, cooling chamber 4 is marked with dashed lines. Microtome 2 possesses a sample holder 6 that is movable up and down. Also provided on the microtome is a knife holder 8 which is arranged in such a way that it is located opposite a sample 10 mounted on sample holder 6. In the exemplary embodiment depicted in FIG. 1, a shared control unit 12 is provided. Control unit 12, microtome 2, and cooling chamber 4 are each connected using an electrical conductor 14. Associated with control unit 12 is a display 16 on which a user interface, for adjusting microtome 2 and cooling chamber 4, is displayed. The user interface makes adjustment icons or buttons for microtome 2 and cooling chamber 4 available to the user. Since it often happens that customers first purchase microtome 2 and later opt for a cooling chamber 4, control unit 12 is designed so that it detects, for example, a cooling chamber that has just been connected, and rearranges or adapts the user interface in accordance with the new configuration of the system. Operating elements that are connected to control unit 12 can assume various configurations. For example, they can be embodied as buttons, rotary encoders, or joysticks, and can have various functions. Also conceivable for display 16 is a touch screen on which, alongside the operating elements for microtome 2, additional or different operating elements for cooling chamber 4 can be displayed. Actuation of the operating elements using external input devices such as a mouse, trackball, etc. is also possible.

FIG. 2 depicts a different exemplary embodiment of the invention. Identical reference characters are used for identical elements. Here control unit 12 is provided in microtome 2, and is hereinafter labeled with the reference character 18. A detection device 20, which is connected to a control unit 18 via a conductor 22, is provided between microtome 2 and cooling chamber 4. Detection device 20 can be embodied as a plug connector, a transponder, a scanner, a barcode reader, etc. In the case of a scanner or barcode reader, a label or a barcode (not depicted) is advantageously provided on cooling chamber 4. The label or barcode are applied on cooling chamber 4 in such a way that when a cooling chamber 4 is placed on a microtome 2, it is located opposite detection device 20. A trackball 24, for example, with which multiple actuation elements for microtome 2 and/or for cooling chamber 4 can be operated on display 16 by the user, is connected to control unit 18. Display 16 itself is connected via a conductor 24 to control unit 18. A wireless connection between display 16 and control unit 18 is also conceivable.

Figure 3:
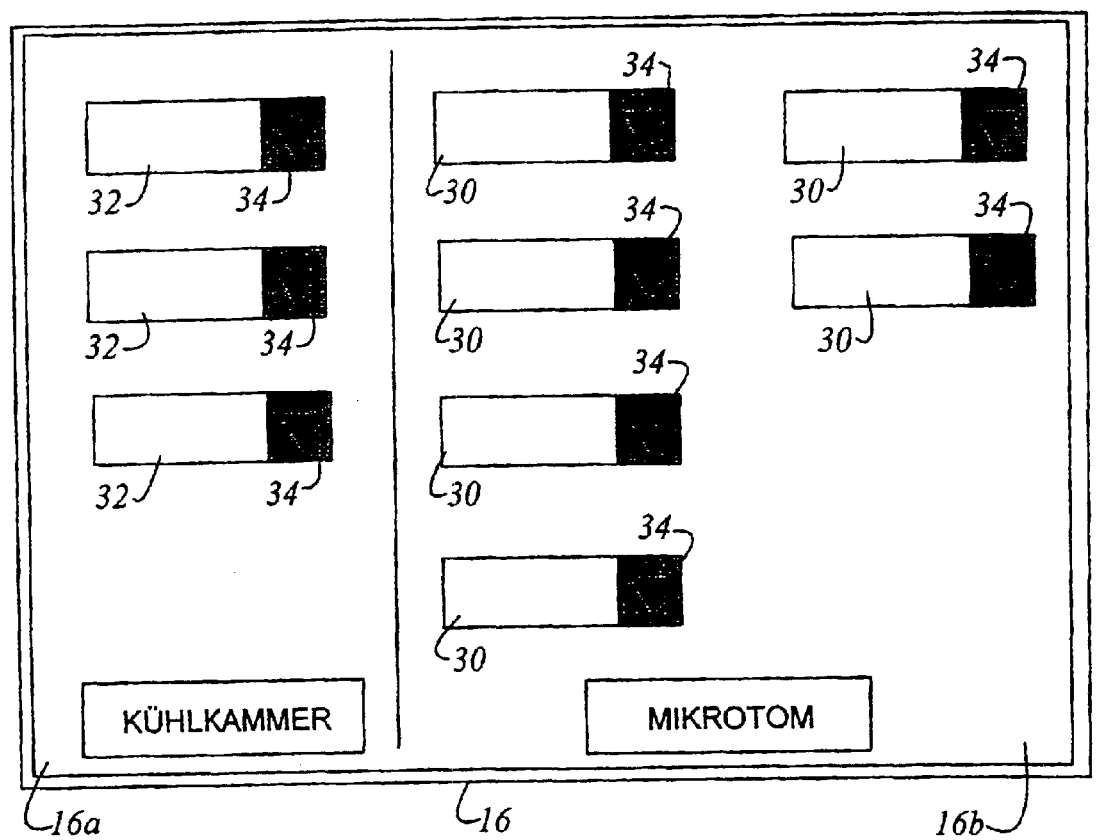
FIG. 3 schematically depicts a user interface for the shared control unit.

FIG. 3 is a schematic depiction of a user interface for the shared control unit 12 or 18. The description below refers to the embodiment depicted in FIG. 3, but it is self-evident that this is not to be construed as a limitation. Multiple operating elements 30 for microtome 2, and multiple operating elements 32 for cooling chamber 4 if applicable, are displayed on display 16. FIG. 3 depicts the situation in which a cooling chamber 4 is connected to microtome 2. Control unit 12 or 18 detects the cooling chamber, so that display 16 is divided by means of a software program into a first part 16a and a second part 16b. Operating elements 32 for cooling chamber 4 are displayed in first part 16a, and operating elements 30 for microtome 2 in second part 16b. Operating elements 32 for cooling chamber 4 can encompass, for example, setpoint temperature, actual temperature, cooling rate, etc. Operating elements 30 for microtome 2 can encompass, for example, cutting speed, sample feed, etc. Operating elements 30 and 32 can be equipped with a pull-down menu 34 with which the user can select defined parameter increments or also make user-defined inputs.

What is claimed is:

1. An apparatus for controlling a microtome and a cooling chamber, which is positioned on the microtome, comprising:
   a single control unit that integrates both operating elements for the microtome and operating elements for the cooling chamber;
   a single display or screen is associated with the control unit, wherein the single display is, dependent from the specific configuration of microtome and cooling chamber, a user interface for the microtome and/or the cooling chamber, and
   wherein a detection device is provided that is connected to the control unit and detects a cooling chamber connected to the microtome, and thereby invokes the set of operating elements for the cooling chamber present in the control unit.

2. The apparatus as defined in claim 1, wherein on the display or screen the operating elements are presented to a user.

3. The apparatus as defined in claim 1, wherein the control unit is configured in such a way that a cooling chamber connected to the microtome is visible on the display; and the control unit modifies or adds to the operating elements presented on the display in accordance with the operating elements for the cooling chamber.

4. The apparatus as defined in claim 1, wherein at least one input device is connected to the control unit so that the operating elements are assigned in user-defined fashion.

5. The apparatus as defined in claim 4, wherein the input device is a mouse, a trackball, a keyboard, a PDA, a touch screen, or a joystick.

6. An apparatus for controlling a microtome and a cooling chamber, which is positioned on the microtome, comprising:
   a single control unit that integrates both operating elements for the microtome and operating elements for the cooling chamber;
   a single display is associated with the control unit, wherein the single display is, dependent from the specific configuration of microtome and cooling chamber, a user interface for the microtome and/or the cooling chamber; and
   wherein a detection device is provided that is connected to the control unit and detects a cooling chamber connected to the microtome, and thereby invokes the set of operating elements for the cooling chamber present in the control unit; and
   wherein the detection device is embodied as a plug connector, a transponder, a scanner, or a barcode reader.

* * * * *